BEST AVAILABLE COPY

T862,005

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED MAY 6, 1969

862 O.G. 22

670,757

1-(α,α-DISUBSTITUTED METHYLENE) - 3-INDANONES AND -INDANES FROM INDAN-1,3-DIONES

Gether Irick, Jr., % Tennessee Eastman Company, P.O. Box 511, Kingsport, Tenn. 37662

Filed Sept. 26, 1967. Published May 6, 1969
Int. Cl. C09b *23/04, 23/06, 23/10*
U.S. Cl. 260—240
No Drawing. 38 Pages Specification

Novel indanone compounds containing a cyanomethylidene group and derivatives thereof which are useful as textile dyes have the formula

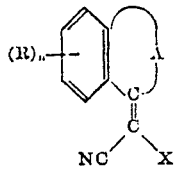

wherein

A is a group having the formula

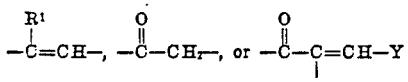

in which the carbon atom bearing the substituent $R^1$ or the carbonyl carbon atom is attached to the benzene nucleus and wherein $R^1$ is a halogen, lower alkoxy, cyclohexoxy, a phenoxy group, or an amino group

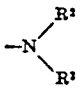

wherein $R^1$ and $R^2$ when taken singly are the same or different and each represents hydrogen; lower alkyl; lower alkyl substituted with halogen or hydroxy; phenyl; phenyl substituted with lower alkyl, lower alkoxy, or halogen; or cyclohexyl or

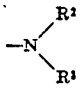

collectively represent N-methyl-piperazino, pyrrolidino, lower alkylpyrrolidino, piperidino, lower alkyl piperidino, morpholino, lower alkylmorpholino, 4-thiomorpholino - 1,1 - dioxide, 1,2,3,4 - tetrahydroquinolino, or lower alkyl-1,2,3,4-tetrahydroquinolino;

Y is the residue of an aromatic aldehyde having the formula

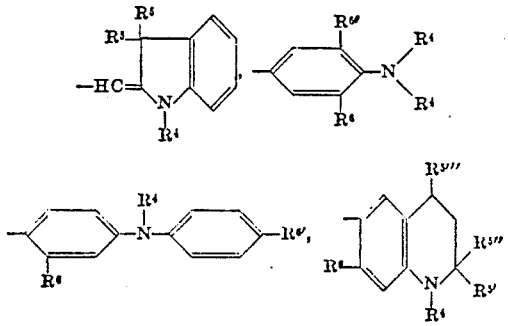

or

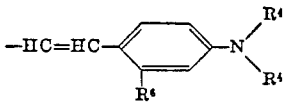

wherein $R^4$ is a lower alkyl group or a phenyl group;

$R^5$ is lower alkyl; $R^{5'}$, $R^{5''}$, and $R^{5'''}$ are the same or different and each represents hydrogen or lower alkyl; and $R^6$ and $R^{6'}$ are the same or different and each represents hydrogen, lower alkyl, lower alkoxy, halogen, lower alkylthio, lower dialkylamino, nitro or cyano;

R is hydrogen, lower alkyl, lower alkoxy, phenoxy, phenylthio, lower alkylthio, lower alkylsulfonyl, cyano, nitro, or halogen;

*n* is 1 or 2; and

X is phenyl; phenyl substituted with lower alkyl, lower alkoxy, or halogen; cyano; carbamoyl; lower alkylcarbamoyl; lower alkoxycarbonyl; lower alkamoyl; benzoyl; or benzoyl substituted with lower alkyl, lower alkoxy or halogen.